United States Patent [19]

Swendson et al.

[11] Patent Number: 5,354,272

[45] Date of Patent: Oct. 11, 1994

[54] IMPROVED INJECTATE DELIVERY SYSTEM

[75] Inventors: David L. Swendson, Garden Grove; David J. Evans, Irvine; Lucien Attal, Anaheim, all of Calif.

[73] Assignee: Baxter International Inc., Deerfield, Ill.

[21] Appl. No.: 25,002

[22] Filed: Mar. 2, 1993

[51] Int. Cl.$^5$ ............................................. A61M 31/00
[52] U.S. Cl. .................................................... 604/65
[58] Field of Search ............................. 137/896, 897; 604/31-34, 66, 65, 245

[56] References Cited

U.S. PATENT DOCUMENTS

| | | | |
|---|---|---|---|
| 4,103,686 | 8/1978 | LeFevre | 128/214 R |
| 4,246,932 | 1/1981 | Raines | 137/512 |
| 4,310,017 | 1/1982 | Raines | 137/533 |
| 4,535,820 | 8/1985 | Raines | 137/854 |
| 4,540,027 | 9/1985 | Forberg | 137/848 |
| 4,556,086 | 12/1985 | Raines | 137/852 |
| 4,580,573 | 4/1986 | Quinn | 128/657 |
| 4,626,243 | 12/1986 | Singh et al. | 604/141 |
| 4,683,916 | 8/1987 | Raines | 137/854 |
| 4,703,759 | 11/1987 | Merrick et al. | 128/673 |
| 4,729,401 | 3/1988 | Raines | 137/512 |
| 4,915,688 | 4/1990 | Bischof et al. | 604/83 |
| 4,919,167 | 4/1990 | Manska | 137/512 |
| 5,022,422 | 6/1991 | di Palma | 137/15 |
| 5,037,390 | 8/1991 | Raines et al. | 604/83 |
| 5,098,405 | 3/1992 | Peterson et al. | 604/247 |
| 5,127,904 | 7/1992 | Loo et al. | 604/83 |
| 5,221,271 | 6/1992 | Nicholson | 604/283 |

FOREIGN PATENT DOCUMENTS

| | | |
|---|---|---|
| 0489297A1 | 11/1991 | European Pat. Off. . |
| 3503320 | 8/1986 | Fed. Rep. of Germany . |
| 3503320A1 | 8/1986 | Fed. Rep. of Germany . |
| 3518575A1 | 10/1986 | Fed. Rep. of Germany . |

Primary Examiner—Jerome L. Kruter
Attorney, Agent, or Firm—Bruce M. Canter

[57] ABSTRACT

An improved integral flow-through injectate delivery system comprises fluid flow means having a proximal and a distal end. The proximal end comprises a first port having fluid inlet means for connecting the flow means to a source of fluid injectate and a second port adapted to be connected to a syringe means. The distal end of the fluid flow means is adapted to be connected to a fluid delivery means for delivering the injectate to the patient and the syringe means is adapted to direct injectate fluid from the injectate source through the fluid inlet and the fluid flow means to the fluid delivery means. A first check valve is in fluid-flow communication with the fluid inlet means and the fluid flow means and a second check valve means is in fluid-flow communication with the fluid flow means and the fluid delivery means. A sensing means is disposed within the fluid flow means at its distal end for sensing a characteristic of fluid flowing therethrough, usually temperature. A fluid flow regulating means is placed within the fluid flow means between the fluid inlet means and the sensing means to delay or limit injectate from flowing therethrough except when being directed by the syringe means.

18 Claims, 5 Drawing Sheets

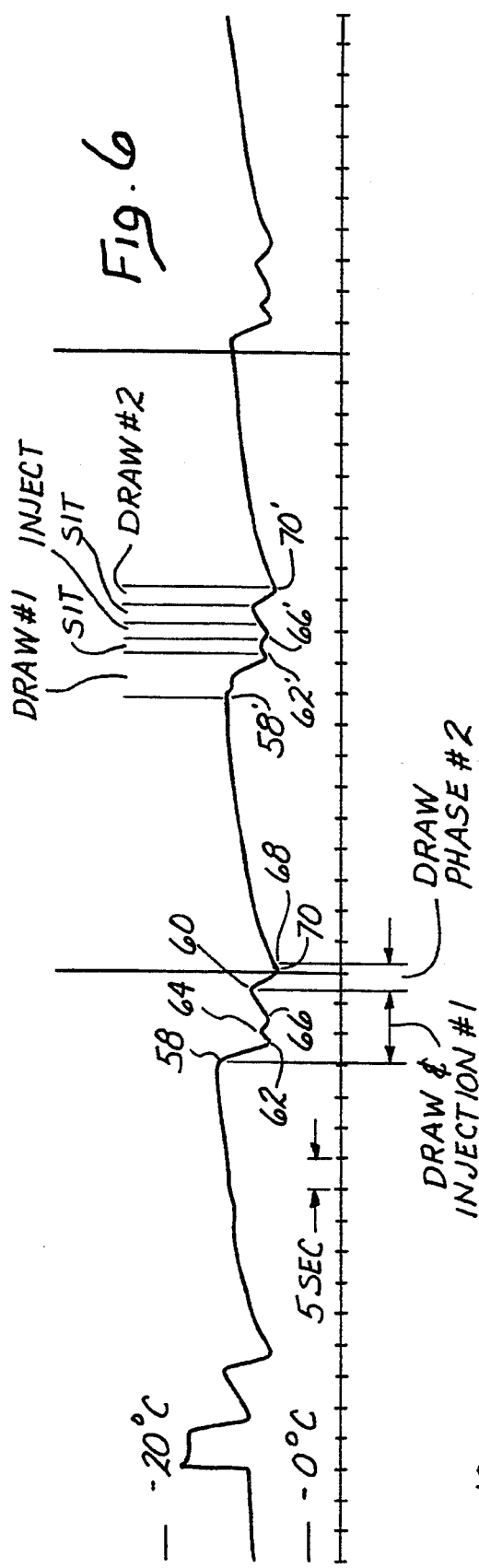
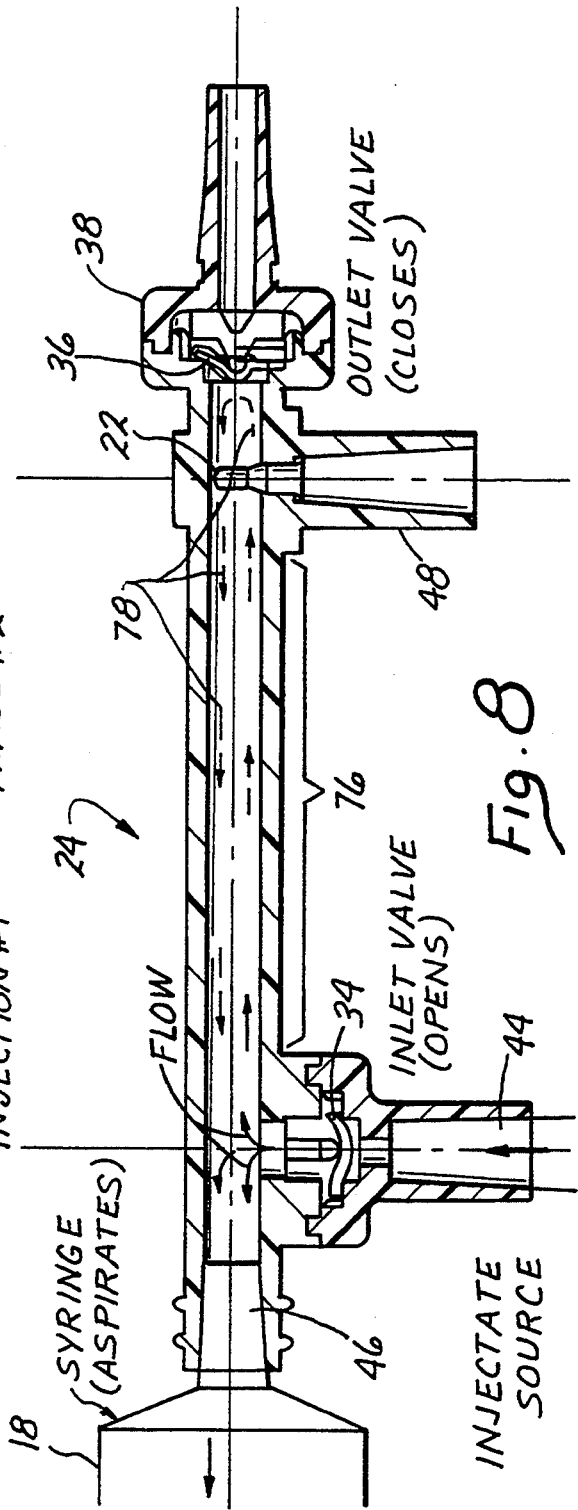

IMPROVED INJECTATE DELIVERY SYSTEM

BACKGROUND OF THE INVENTION

1. Field of the Invention

The invention relates to fluid delivery systems. In particular, the invention relates to new and useful improvements in an apparatus for delivering injectate to patients in medical applications.

2. Discussion of the Prior Art

In various medical contexts, it is important to be able to control the delivery of an injectate fluid to a patient. In one particular medical procedure, known as bolus thermodilution, it is particularly important to accurately monitor the temperature of the injectate as it enters the patient in order to accurately calculate the patient's cardiac output. This well known technique for measuring cardiac output is disclosed in U.S. Pat. No. 4,508,123, to Wyatt et al., which has been assigned to the predecessor of the current assignee, the entire disclosure of which is incorporated herein by this reference.

As discussed in the prior art system of Wyatt et al., a thermodilution injectate assembly includes a length of flexible tubing with a catheter attached thereto for introducing fluid to the patient, an insulated container for cooling the fluid, a temperature probe at the proximal end of the catheter, a temperature probe at the distal end of the catheter, a syringe, and a three-ported stopcock in fluid communication with the fluid container, the flexible tubing and the syringe. The syringe is utilized to draw cooled fluid from the container and inject the fluid through the flexible tubing into the patient. The stopcock is utilized to create a flow through path either between the syringe and the container, or between the syringe and the flexible tubing. The first temperature probe is used to measure the temperature of the injectate as it enters the patient and the second temperature probe is used to measure downstream temperature. The change in fluid temperature is used to calculate cardiac output according to well known principles, as described in Wyatt et al.

One disadvantage of the system of Wyatt et al., is the need for the three-way stopcock. The operator of the system must first manually turn the stopcock to a first position to permit fluid to fill the syringe and then manually turn the stopcock to a second position to permit fluid flow from the syringe into the patient.

In an improved prior art system utilized by the applicant's assignee, Baxter International Inc., a dual directional check valve assembly is utilized in place of the stopcock of Wyatt et al. Such a check valve assembly is disclosed in U.S. Pat. No. 4,210,173, to Choksi et al., which has been assigned to the predecessor of the current assignee, the entire disclosure of which is incorporated herein by this reference. As disclosed therein, flexible, resilient discs are placed on opposite ends of flexible tubing between the fluid inlet and the fluid outlet respectively.

The use of the Choksi et al. assembly with the Wyatt et al. system permits the syringe to withdraw injectate from the container during its withdrawal stroke and inject it into the patient during its injectate stroke, without the need for a stopcock. During the syringe withdrawal stroke, the check valve between the fluid container and the syringe is opened and the check valve between the syringe and the outlet is closed. During the syringe injection stroke, the check valves are in the opposite configuration.

In this improved system, the check valve assembly is an integral unit which is connectable at its distal end, via a flow-through fitting, to the proximal end of the catheter. The proximal end of the assembly has two ports, one which is connectable to the injectate source and one which is connectable to the syringe. In this system, the temperature probe is placed just distal to the flow-through fitting at the proximal end of the catheter tubing.

The aforementioned system has many disadvantages, among which are the number of tubing connections, the number of fluid connections, the difficulty in handling, and the increased manufacturing cost.

Accordingly, it is an object of the invention to provide an efficiently designed integral flow through injectate assembly.

Further objects of the invention are to provide a flow through injectate assembly that is easy and inexpensive to manufacture, that is easy to handle and that has less flow path connections.

Yet a further object of the invention is to provide a flow through injectate assembly that permits accurate sensing of the injectate flowing therethrough.

SUMMARY OF THE INVENTION

These and other objects of the invention are achieved by the integral flow-through injectate assembly of the present invention which, in accordance with broad structural aspects thereof, includes an integral housing comprising an injectate inlet port, an injectate outlet port, a syringe port, a first check valve, a second check valve, a temperature probe receiver, and a fluid flow regulating means. The first and second check valves are utilized, in the fashion described above, so that injectate is only permitted to flow as directed by the syringe, without the need for a stopcock.

In the present invention, the temperature probe receiver, instead of being placed distal to the second check valve, is placed within the integral check valve housing assembly itself. This construction permits the temperature probe receiver to be in the same assembly as the injectate assembly, thus eliminating the need for a separate flow-through fitting.

In accordance with yet another feature of the present invention, a fluid flow regulating means is interposed between the injectate inlet port and the temperature receiving means, limiting injectate flow towards the temperature probe receiver, except when being so directed by the syringe. The regulating means can be anything that disturbs or slows fluid flow in the assembly so that injectate flow towards the probe receiver is proscribed or limited. In a preferred embodiment, the regulating means is a fluid deflecting means which limits the amount of fluid which will migrate towards the temperature probe during the syringe withdrawal stroke, thereby preventing thermal contamination of fluid at the probe. In another embodiment, the regulating means is an extended fluid pathway between the injectate inlet port and the temperature receiving means.

Other features and advantages of the present invention will become apparent from the following detailed description, taken in conjunction with the accompanying drawings which illustrate, by way of example, the principles of the present invention.

BRIEF DESCRIPTION OF THE DRAWINGS

FIG. 6 is a graph of the measured injectate temperature probe values over time utilizing the assembly of FIG. 5;

FIG. 8 is an enlarged cross-sectional view of an alternate embodiment of the integral flow-through injectate assembly of the present invention;

DETAILED DESCRIPTION OF THE INVENTION

Figure 1:
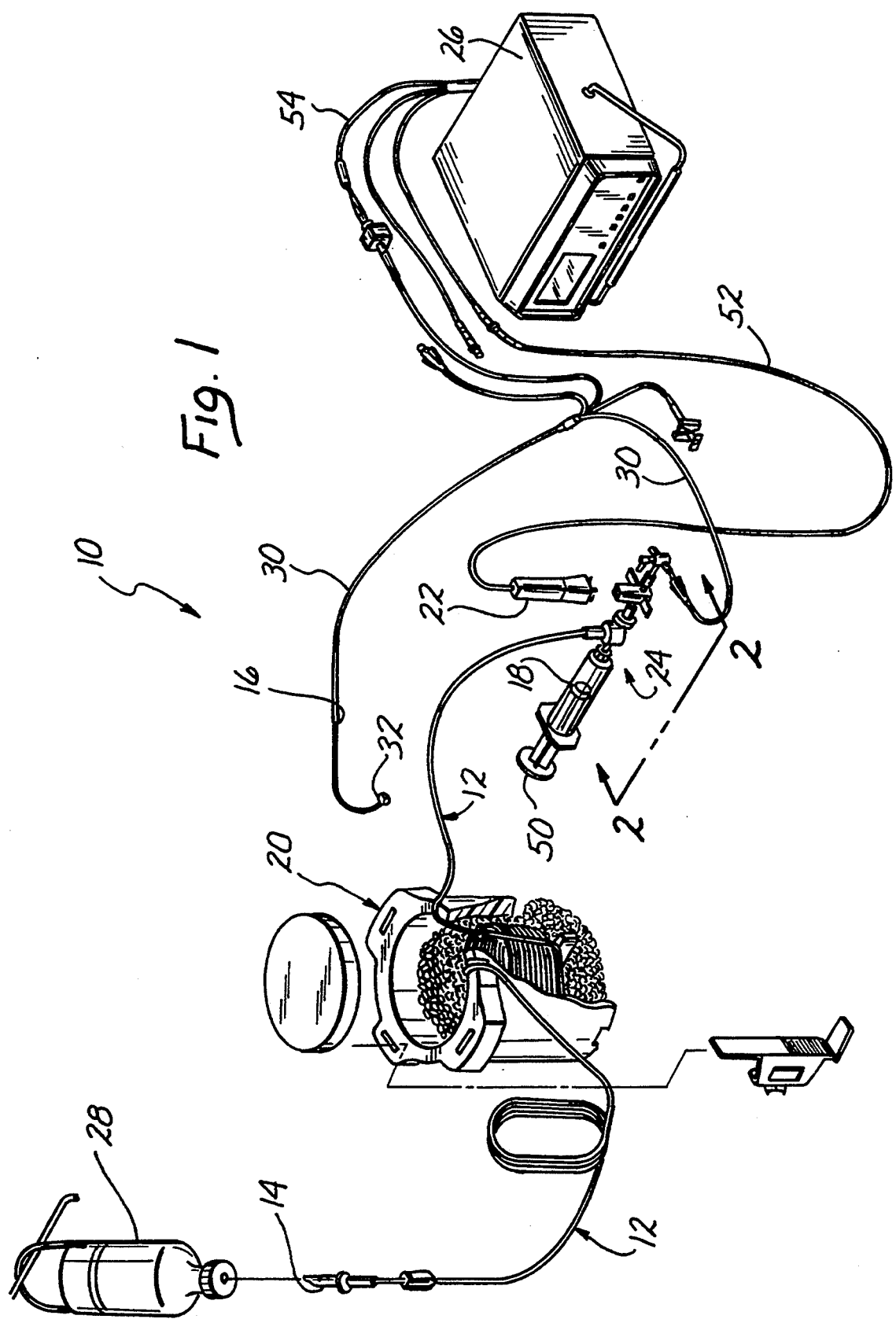
FIG. 1 is a schematic perspective view of a thermodilution injectate system.

FIG. 1 refers to a typical thermodilution system 10 for use in measuring the cardiac output of a patient. The system 10 includes a conduit 12 having an inlet 14 and an outlet 16, a pump in the form of a syringe 18, a cooling container 20, a temperature probe 22, a flow-through assembly 24 adapted to cooperate with the probe 22, and a cardiac output computer 26.

As described more specifically in Wyatt et al., system 10 is utilized to inject a cooled injectate into a patient and to measure the temperature changes downstream in order to calculate cardiac output according to well known thermodilution techniques and principles. In the particular thermodilution system 10 of FIG. 1, cooling container 20 is used to cool saline from saline bottle 28 which travels along conduit 12 into container 20. Syringe 18 is used to pump the cooled saline through conduit 12 and into the patient (not shown) as hereinafter described. The distal end of flow-through assembly 24 is coupled to a thermodilution catheter 30 which forms part of conduit 12 and which includes balloon 32 at its distal end. Balloon 32 is typically placed in the pulmonary artery of the patient so that outlet port 16, which is just proximal to balloon 32, is placed in the right atrium of the patient's heart to permit the cooled saline to mix with the patient's blood.

Temperature probe 22 is coupled to flow-through assembly 24 to sense the temperature of the cooled saline as it is injected into the patient. Probe 22 is also coupled to cardiac output computer 26, to which it transmits a signal representing the injectate temperature. Adjacent to balloon 32 is a downstream thermistor (not shown) which measures the temperature of the blood-injectate mixture after it is pumped through the atrium. The thermistor is also coupled, via catheter 30, to cardiac output computer 26, which processes temperature data from probe 22 and from the downstream thermistor to calculate cardiac output.

Figure 2:
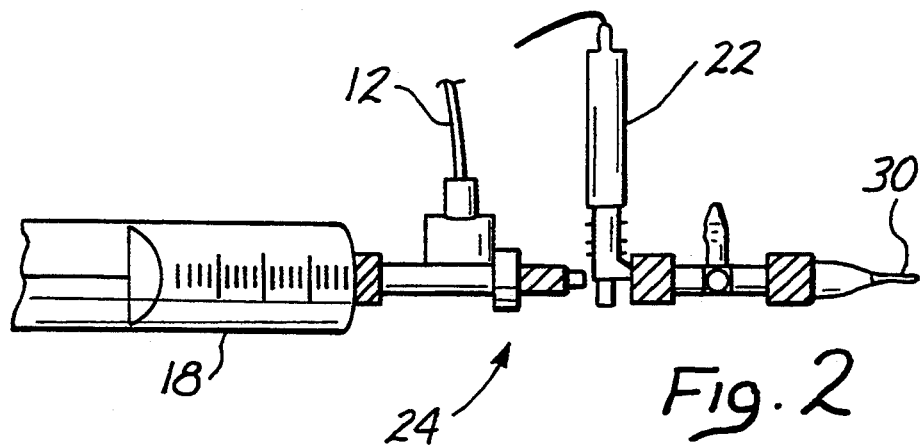
FIG. 2 is a partial cross-sectional view of the injectate assembly portion of the system of FIG. 1, taken along lines 2—2.

FIG. 2 illustrates flow-through assembly 24 of system 10 which is attached to syringe 18 and conduit 12. Syringe 18 draws fluid from container 20 through conduit 12 and into catheter 30. Temperature probe 22 is attached to the distal end of assembly 24 to monitor temperature that is directed through assembly 24 to catheter 30, and ultimately into the patient.

Figure 3:
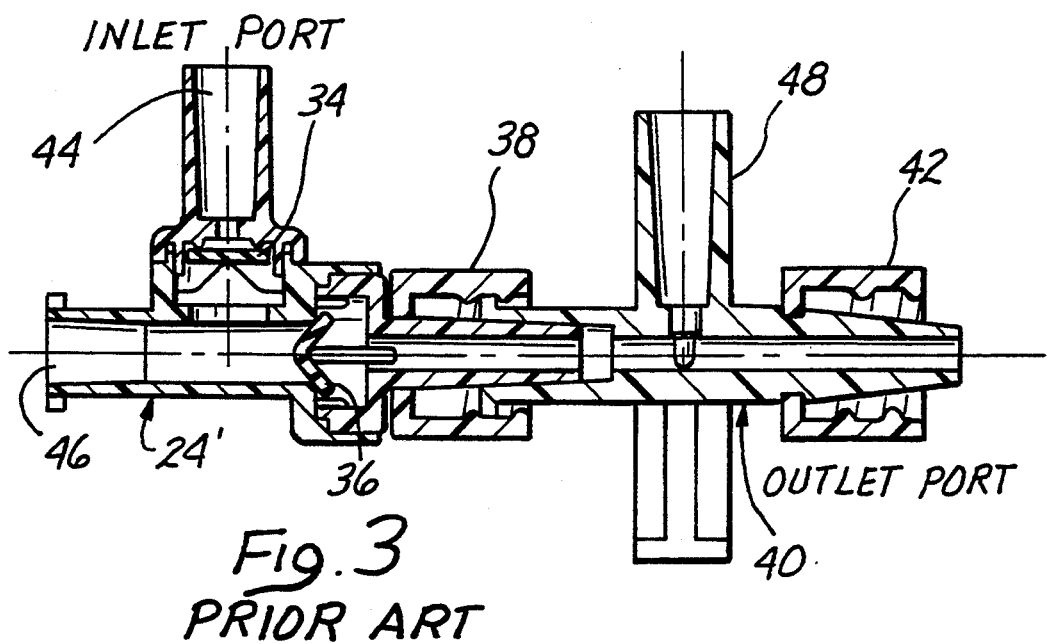
FIG. 3 is a cross-sectional view of a prior art version of a flow-through injectate assembly.

FIG. 3 illustrates a prior art flow-through assembly 24' that is usable with system 10. Assembly 24' is comprised of first check valve 34 and second check valve 36, as disclosed in U.S. Pat. No. 4,210,173, to Choksi et al., which are part of an integral unit connectable at its distal end, via first flow-through fitting 38, to temperature probe housing 40. Housing 40 is connectable at its distal end, via second flow-through fitting 42, to the proximal end of catheter 30. The proximal end of assembly 24' has a first assembly port 44 which is in fluid communication with cooled container 20 through conduit 12, and a second assembly port 46 which is connectable to the syringe. In this system, temperature probe 22 is placed in temperature probe receiving means 48, which is disposed within temperature probe housing 40, distal to first flow-through fitting 38 and proximal to second flow-through fitting 42. As discussed above, the number of tubing connections and fluid connections renders this system difficult to handle and expensive to manufacture.

Figure 4:
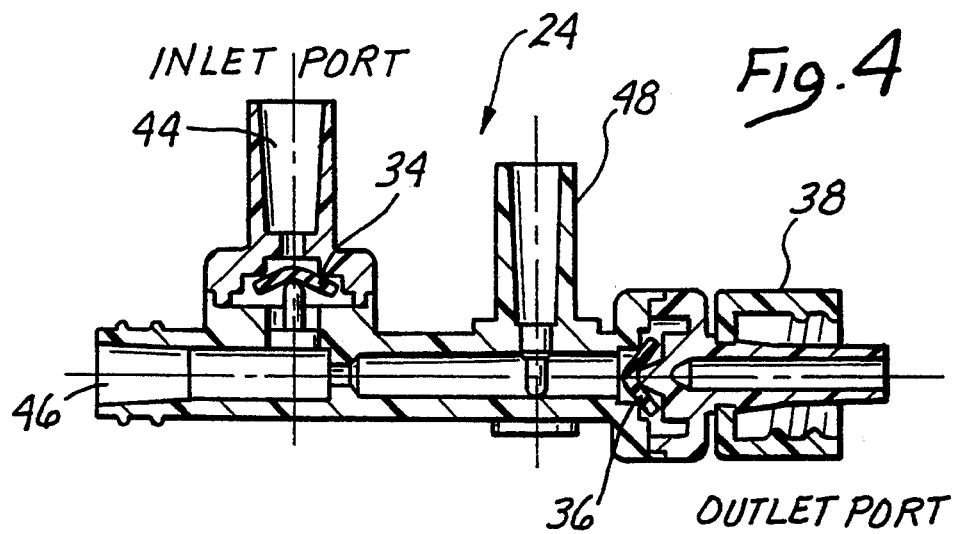
FIG. 4 is a cross-sectional view of the flow-through injectate assembly of the present invention.

FIG. 4 illustrates the improved injectate flow through assembly 24 of the present invention which overcomes some of the disadvantages of prior art systems. First and second check valves 34 and 36 are again utilized to control fluid flow as described above and are part of an integral flow through assembly 24. In the present invention, however, temperature probe receiving means 48 is part of integral assembly 24 and is placed just proximal to the second check valve 36. Assembly 24 is thus directly coupled to catheter 30 through flow-through fitting 38. Since temperature probe housing 40 and second flow-through fitting 42 have been eliminated, the number of tubing and fluid connections is reduced.

Syringe 18, which is attached to assembly 24 at port 46 is utilized to draw cooled fluid, like saline, from cooled container 20 and inject the fluid through catheter 30 into the patient through outlet 16. Temperature probe 22, which is placed in temperature probe receiving means 48, measures the temperature of the fluid as it enters catheter 30. Catheter 30 is made of thermally insulated material which is sufficient to maintain the fluid at a fairly constant temperature until it exits outlet 16.

The advantages of the present invention will become apparent to those skilled in the art from the more detailed discussion that follows. Prior to undertaking the thermodilution procedure, saline is permitted to drip from bottle 28 through inlet 14 to conduit 12 and into cooled container 20 where it is chilled to a preferred temperature. Syringe 18 has, up to now, been in a closed position. Plunger 50 of syringe 18 is withdrawn and saline is drawn from cooled container 20 into syringe 18. The saline is injected into the patient through port 16 of catheter 30 by pushing plunger 50 back into syringe 18. Temperature probe 22, which has been placed into temperature probe receiving means 48, measures the temperature of the saline injectate which is transmitted to cardiac output computer 26 via cable 52. As discussed above, a thermistor (not shown) is placed at the distal end of catheter 30 to measure the temperature of the blood and saline mixture which has been pumped through the auricle. The thermistor is connected to computer 26 via thermistor cable 54 through which it transmits the temperature reading. The computer 26 is then able to compute the patient's cardiac output according to well known principles.

Figure 5:
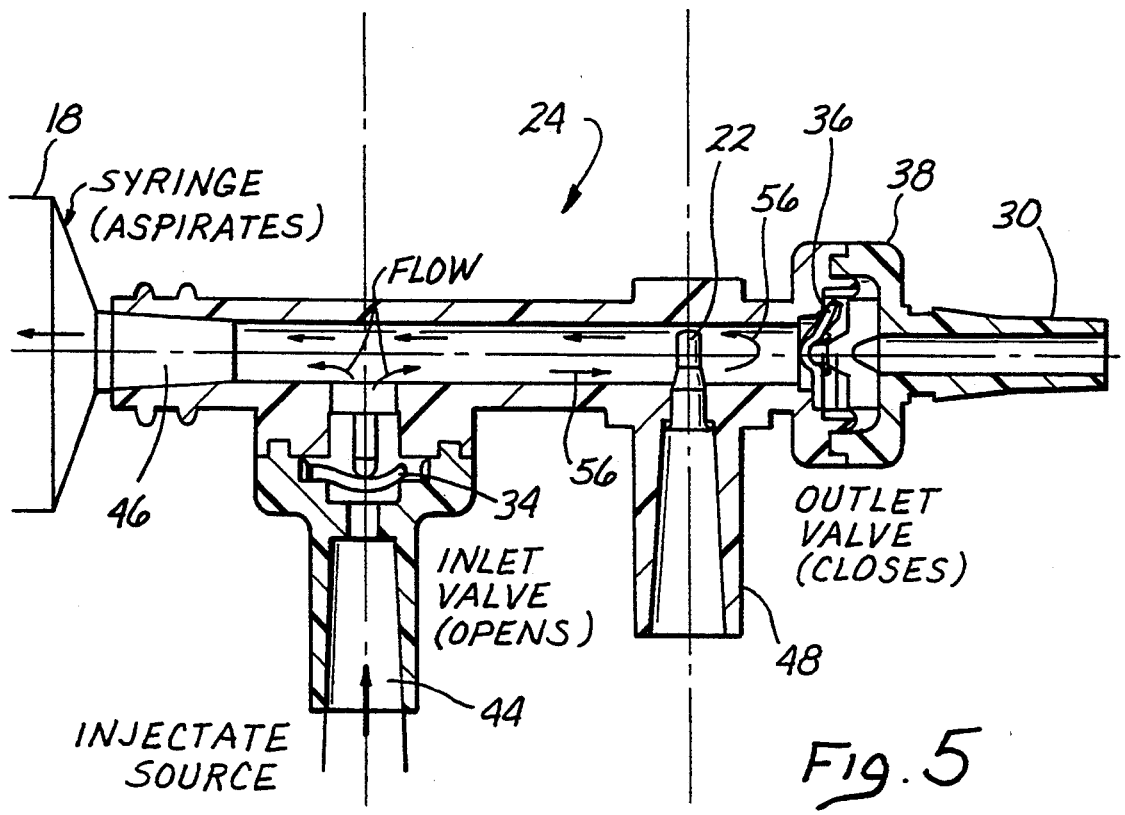
FIG. 5 is an enlarged cross-sectional view of an integral flow-through injectate assembly without a deflection means.

In order for the cardiac output calculation to be accurate, the initial temperature measurement by temperature probe 22 must be within a certain range of accuracy. Computer 26 is programmed to utilize the lowest temperature sensed by probe 22. A problem that arises consequent to having temperature probe receiving means 48 as an integral part of assembly 24 is the tendency for probe 22 to sense fluid of different temperature that may migrate within the assembly. The potential problem occurs after saline is injected into the patient and cold saline is then immediately withdrawn into the syringe again. The flow of saline from port 44 to syringe 18, as well as the migration of some saline to probe 22, is illustrated by arrows 56 in FIG. 5.

When, immediately after injection, plunger 50 is withdrawn back into syringe 18 to draw a new supply of saline through port 44, some saline may migrate towards temperature probe 22 causing thermal contamination. Computer 26 will detect the temperature of the migrated saline, utilizing this lower temperature in calculating cardiac output. Since the temperature of the contaminated saline is lower than that of the previously injected saline, the cardiac output calculation is based upon an erroneous temperature baseline.

FIG. 6, a graph of the measured injectate temperature probe values versus time, illustrates the aforementioned problem. The curve between points 58 and 60 shows the temperature variation of the injectate during a first draw and injection and a short waiting period thereafter. Point 58 is the point of highest temperature before drawing the saline for the first injection, which is also used by computer 26 to define the baseline temperature. The curve between points 58 and 62 shows the injectate temperature variation, due to thermal contamination, during the draw phase of the first injection. Points 62 to 64 show a short waiting period just prior to the first injection. The curve between points 64 and 66 represents the actual injection phase of the first injection, with point 66 representing the true injectate temperature. Thus, computer 26 should utilize the lowest temperature at point 66. The curve between points 66 and 60 represents the elapsed time between the first injection and the draw phase for the second injection.

The problem becomes evident with reference to the following curve segment. Points 60 through 68 represent the temperature variation during the draw phase for the second injection, which immediately succeeds the first injection. Point 70, which is the temperature of the contaminated saline, displays a lower temperature than point 66 and causes computer 26 to reset the baseline temperature it used to calculate cardiac output for the first injection. Point 70, which becomes the new baseline for the cardiac output calculation, does not accurately reflect the lowest temperature of the injected fluid, resulting in an inaccurate thermodilution calculation. Points 58', 62', 66', and 70' illustrates another draw, injection, draw cycle wherein low temperature point 70' is erroneously utilized by computer 26.

Figure 7:
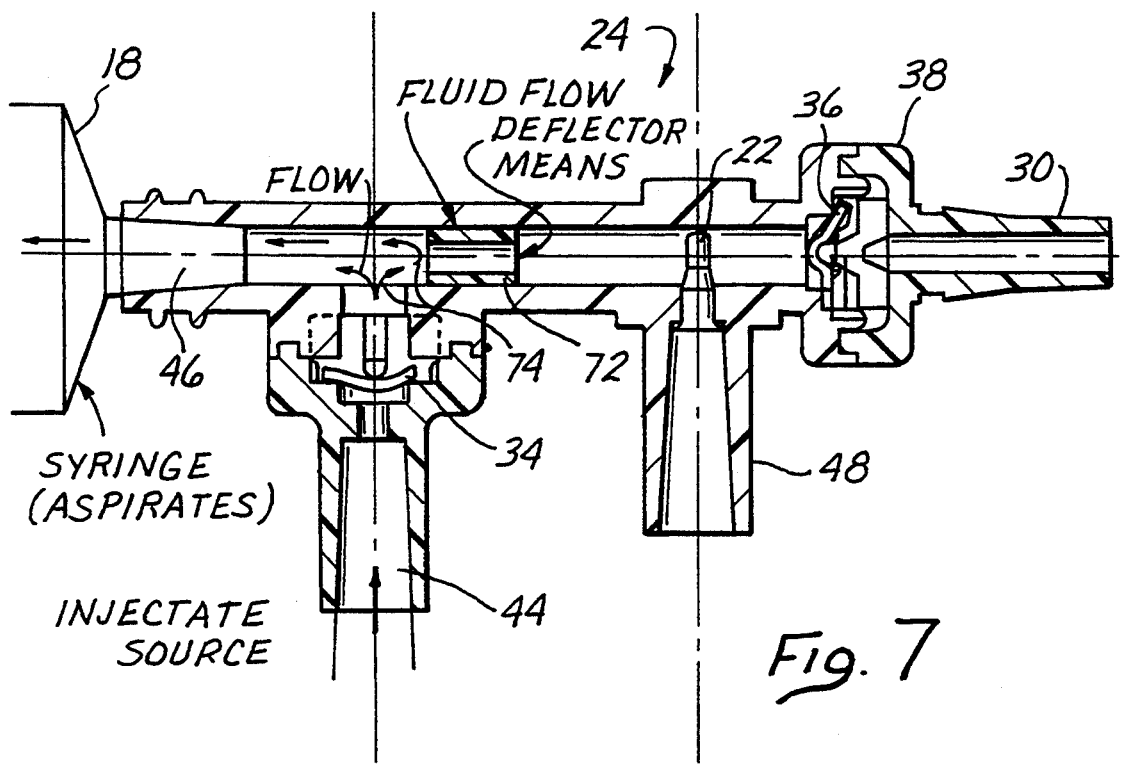
FIG. 7 is an enlarged cross-sectional view of a preferred embodiment of the integral flow-through injectate assembly of the present invention.

One of the features of the present invention is a fluid flow regulating means which is used to interrupt or minimize the migrating fluid so that there is no significant thermal contamination during a withdrawal stroke. In a preferred embodiment, the regulating means is a fluid deflection means. This embodiment is illustrated in FIG. 7. A fluid flow deflector means 72 is placed distal from first port 44 at a proximal distance from probe receiving means 48. Deflector means 72 inhibits fluid particles, as indicated by arrows 74 from migrating distally along assembly 24. Deflector means 72 could be a roughened or grooved surface along the interior surface of assembly 24, or a series of bumps along the surface. Any means of creating a disruption in fluid flow would function as a deflector to limit the amount of fluid which migrates towards probe receiving means 48 and probe 22. In a preferred embodiment, deflector means 72 is a narrowed orifice that reduces the cross-sectional flow area of the cooled fluid in assembly 24. However, those skilled in the art will appreciate that deflector means 72 could be any of the means for creating a disruption of flow as discussed above, as well as other equivalents.

In yet another embodiment of the present invention, as illustrated in FIG. 8, the regulating means is an extended flow path 76 between injectate port 44 and temperature probe receiving means 48. Increasing the distance between these points reduces the thermal effect of the migrated fluid so that it will not significantly contaminate probe 22. By the time the saline has migrated to probe 22, as shown by arrows 78, it will have warmed sufficiently so that it does not significantly contaminate probe 22.

Figure 9:
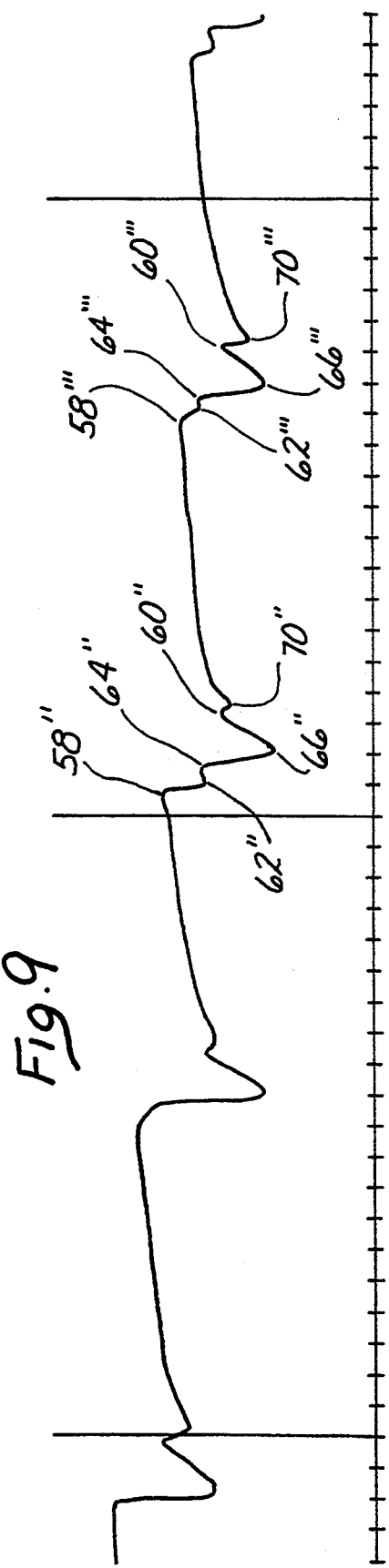
FIG. 9 is a graph of the measured injectate temperature probe values over time utilizing the assembly of FIG. 7.

FIG. 9 is a graph of the measured injectate temperature probe values versus time utilizing assembly 24 of the present invention, as illustrated in FIG. 7. Points 58" and 60" are the end points of the temperature versus time curve during a fluid injection and a short waiting period thereafter. Points 58" through 62" represent the injectate temperature variation during the first draw. Points 62" through 64" represent a short waiting period and points 64" through 66" represent the actual injection, with point 66" indicating the lowest temperature point. Points 66" through 60" represent a short waiting period prior to the second draw and points 60" through 70" represent the second draw.

Figure 10:
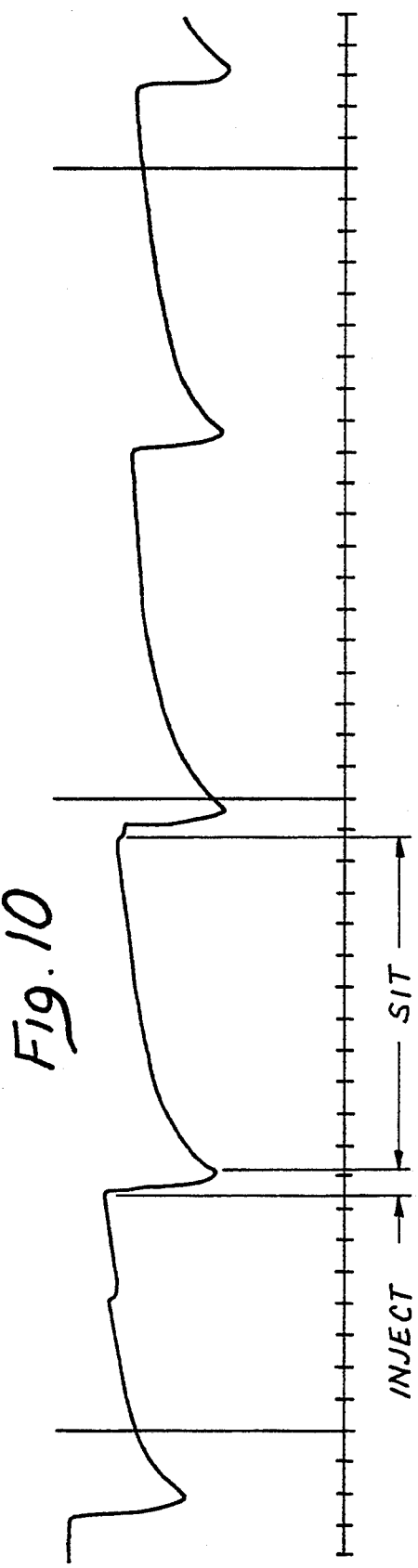
FIG. 10 is a graph of the measured injectate temperature probe values over time utilizing a prior art injectate assembly.

Note that there is no point along the curve between points 60" and 70" that is lower than point 66", which represents the actual injectate temperature. Thus, computer 26 will accurately utilize point 66" as its baseline injectate temperature point. It is not until a further fluid injection is made that a similarly low temperature point is reached, as illustrated by point 66'". Thus, with the present invention, there is no significant thermal contamination during the second draw period. FIG. 10 graphically illustrates the use of a prior art injectate assembly. A comparison of FIG. 9 with FIG. 10 graphically illustrates that the injectate assembly of the present invention performs as well as the cumbersome prior art injectate flow assemblies, which have the disadvantages discussed above. The assembly utilized in FIG. 10 is of the type illustrated in FIG. 3, wherein temperature probe 22 is distal from check valve 36 and thereby insulated from migrating fluid. A comparison of the curves illustrated in FIG. 9 and 10 indicate that in both cases the lowest temperature measurements occur during the injectate stroke, assuring a more accurate thermodilution calculation. FIGS. 9 and 10 show that the integrated assembly of the present invention operates as effectively as the prior art, two part assembly of FIG. 3.

Thus, it has been shown that it is possible to integrate the assembly, with the attendant benefits in cost, ease of manufacturing, reduction in connections, etc., and still provide for an accurate thermodilution calculation.

In closing it is to be understood that the embodiments of the invention disclosed herein are illustrative of the principles of the invention and that other modifications may be employed which are within the scope thereof. Accordingly, the present invention is not limited to that precisely as shown and described in the specification, and any modifications, variations or equivalent arrangements within the scope of the attached claims should be considered to be within the scope of the invention.

What is claimed is:

1. A fluid flow delivery system for delivering injectate fluid to a patient comprising:
    fluid flow means having a proximal and a distal end, wherein said proximal end comprises a first port having fluid inlet means for connecting said flow means to a source of fluid injectate and a second port connected to a syringe means, and said distal end comprises a port for connecting said fluid flow means to a fluid delivery means for delivering the injectate to the patient;
    wherein said syringe means is in fluid-flow communication with said injectate source through said fluid inlet means and is in fluid-flow communication with said fluid flow means through said second port, and said fluid flow means is in fluid-flow communication with said fluid delivery means;
    sensing means disposed within said fluid flow means at its distal end for sensing a characteristic of fluid flowing therethrough; and
    fluid flow regulating means interposed between said fluid inlet means and said sensing means, for delaying said injectate from contacting said sensing means;
    wherein said fluid flow means, said sensing means and said fluid flow regulating means are part of an integral fluid flow assembly.

2. The fluid flow delivery system of claim 1 wherein said fluid flow regulating means comprises fluid flow deflector means, interposed between said fluid inlet means and said sensing means, for limiting the quantity of injectate which flows therethrough except when being directed by said syringe means.

3. The fluid flow delivery system of claim 2 wherein said fluid inlet means has a certain cross-sectional flow area and said fluid flow deflector means comprises a flow restrictor placed within said first to reduce said cross-sectional flow area.

4. The fluid flow delivery system of claim 2 wherein said fluid flow means has a certain cross-sectional flow area and said fluid flow deflector means comprises a roughened surface along the interior cross-section of said fluid flow means.

5. The fluid flow delivery system of claim 2 wherein said fluid flow means has a certain cross-sectional flow area and said fluid flow deflector means comprises grooves along the interior cross-section of said fluid flow means.

6. The fluid flow delivery system of claim 2 wherein said fluid flow means has a certain cross-sectional flow area and said fluid flow deflector means comprises bumps along the interior cross-section of said fluid flow means.

7. The fluid flow delivery system of claim 1 wherein said fluid flow regulating means comprises an extended flow path between said fluid inlet means and said sensing means, for delaying the injectate from contacting said sensing means.

8. The fluid flow delivery system of claim 7 wherein said sensing means is a temperature sensing means and said extended flow path is of sufficient length so that the injectate does not contaminate said temperature sensing means.

9. The fluid flow delivery system of claim 1 wherein said sensing means comprises probe receiving means adapted to receive a probe for sensing a characteristic of fluid flowing through said fluid inlet means.

10. The fluid flow delivery system of claim 1 wherein said sensing means comprises means for receiving a temperature probe for sensing the temperature of fluid flowing through said fluid inlet means.

11. The fluid flow delivery system of claim 1 wherein said sensing means comprises a temperature probe for sensing the temperature of fluid flowing through said fluid inlet means.

12. The fluid flow delivery system of claim 11 wherein said temperature probe is a thermistor.

13. The fluid flow delivery system of claim 1 wherein said system is utilized in a thermodilution technique for measuring cardiac output.

14. The fluid flow delivery system of claim 1 further comprising first check valve means in fluid-flow communication with said fluid inlet means and said fluid flow means.

15. The fluid flow delivery system of claim 14 wherein said first check valve means comprises means to prevent injectate flow from said fluid flow means to said fluid inlet means and to permit injectate flow from said fluid inlet means to said fluid flow means only when directed by said syringe means.

16. The fluid flow delivery system of claim 1 further comprising second check valve means in fluid-flow communication with said fluid flow means and said fluid delivery means.

17. The fluid flow delivery system of claim 16 wherein said second check valve means comprises means to prevent injectate flow from said fluid delivery means to said fluid inlet means and to permit injectate flow from said fluid flow means to said fluid delivery means only when directed by said syringe means.

18. The fluid flow delivery system of claim 1 wherein said fluid delivery system comprises a catheter.

* * * * *